(12) United States Patent
Goldreich

(10) Patent No.: US 7,598,878 B2
(45) Date of Patent: Oct. 6, 2009

(54) METHOD AND DEVICE FOR MEASURING PHYSIOLOGICAL PARAMETERS AT THE WRIST

(76) Inventor: Rami Goldreich, 96 Ayalon Street, 48621 Rosh Ha'ayin (IL)

( * ) Notice: Subject to any disclaimer, the term of this patent is extended or adjusted under 35 U.S.C. 154(b) by 0 days.

(21) Appl. No.: 10/497,169

(22) PCT Filed: Dec. 10, 2002

(86) PCT No.: PCT/IL02/00995

§ 371 (c)(1),
(2), (4) Date: Jun. 9, 2004

(87) PCT Pub. No.: WO03/050643

PCT Pub. Date: Jun. 19, 2003

(65) Prior Publication Data

US 2005/0116820 A1     Jun. 2, 2005

(51) Int. Cl.
    *A61B 5/00* (2006.01)
(52) U.S. Cl. .......... 340/573.1; 340/517; 340/539.1; 600/300; 600/323; 600/340; 600/382; 600/301; 128/903
(58) Field of Classification Search .......... 340/573.1; 600/300, 345, 500, 585, 301, 323, 340, 382; 128/903
See application file for complete search history.

(56) References Cited

U.S. PATENT DOCUMENTS

| | | | |
|---|---|---|---|
| 3,911,899 A * | 10/1975 | Hattes | 600/407 |
| 4,331,154 A | 5/1982 | Broadwater et al. | |
| 4,407,295 A | 10/1983 | Steuer et al. | |
| 4,418,700 A | 12/1983 | Warner | |
| 4,784,152 A * | 11/1988 | Shinoda et al. | 600/503 |
| 4,819,860 A * | 4/1989 | Hargrove et al. | 600/483 |
| 4,952,928 A | 8/1990 | Carroll et al. | |
| 5,045,839 A | 9/1991 | Ellis et al. | |
| 5,410,471 A | 4/1995 | Alyfuku et al. | |
| 5,416,695 A | 5/1995 | Stutman et al. | |
| 5,462,051 A | 10/1995 | Oka et al. | |
| 5,515,858 A * | 5/1996 | Myllymaki | 600/301 |
| 5,544,649 A | 8/1996 | David et al. | |

(Continued)

FOREIGN PATENT DOCUMENTS

DE     10005526     8/2001

(Continued)

OTHER PUBLICATIONS

Yang et al, "Development of the Ring Sensor for Healthcare Automation", *Robotics and Autonomous Systems*, 30:273-281, 2000.

(Continued)

*Primary Examiner*—Daniel Wu
*Assistant Examiner*—Son M Tang
(74) *Attorney, Agent, or Firm*—Kohn & Associates, PLLC

(57) ABSTRACT

A wrist-mounted device for measuring at least one physiological parameter of a subject. The present invention enables such a measurement to preferably be transformed into clinically useful information about the subject. Such information may then optionally be sent to medical personnel, for example at a contact and/or monitoring center, through a gateway device. The gateway device preferably communicates with the wrist-mounted device of the present invention through a wireless communication channel.

32 Claims, 6 Drawing Sheets

U.S. PATENT DOCUMENTS

| | | | |
|---|---|---|---|
| 5,652,570 | A | 7/1997 | Lepkofker |
| 5,669,392 | A * | 9/1997 | Ljungstrom ............... 600/510 |
| 5,771,001 | A | 6/1998 | Cobb |
| 5,772,586 | A | 6/1998 | Heinonen et al. |
| 5,778,882 | A * | 7/1998 | Raymond et al. ........... 600/513 |
| 5,807,267 | A * | 9/1998 | Bryars et al. ............... 600/500 |
| 5,853,005 | A | 12/1998 | Scanlon |
| 5,862,803 | A | 1/1999 | Besson et al. |
| 5,877,675 | A | 3/1999 | Rebstock et al. |
| 5,899,928 | A | 5/1999 | Sholder et al. |
| 5,917,415 | A | 6/1999 | Atlas |
| 5,942,979 | A * | 8/1999 | Luppino .................... 340/576 |
| 6,046,761 | A | 4/2000 | Echerer |
| 6,134,504 | A | 10/2000 | Douglas et al. |
| 6,139,494 | A | 10/2000 | Cairnes |
| 6,160,478 | A * | 12/2000 | Jacobsen et al. ....... 340/539.12 |
| 6,327,495 | B1 | 12/2001 | Iwabuchi et al. |
| 6,348,867 | B1 * | 2/2002 | Myllymaki ............. 340/573.1 |
| 6,353,396 | B1 * | 3/2002 | Atlas ....................... 340/693.9 |
| 6,413,233 | B1 | 7/2002 | Sites et al. |
| 6,443,890 | B1 | 9/2002 | Schulze et al. |
| 6,491,647 | B1 * | 12/2002 | Bridger et al. ............. 600/585 |
| 6,494,829 | B1 * | 12/2002 | New et al. ................. 600/300 |
| 6,616,613 | B1 | 9/2003 | Goodman |
| 6,694,180 | B1 * | 2/2004 | Boesen ..................... 600/547 |
| 6,840,904 | B2 * | 1/2005 | Goldberg ................... 600/300 |
| 6,893,396 | B2 * | 5/2005 | Schulze et al. ............ 600/300 |
| 7,044,911 | B2 * | 5/2006 | Drinan et al. ............. 600/300 |
| 7,285,090 | B2 * | 10/2007 | Stivoric et al. ............ 600/300 |
| 2001/0012916 | A1 | 8/2001 | Deuter |
| 2002/0045808 | A1 | 4/2002 | Ford et al. |
| 2003/0107487 | A1 | 6/2003 | Korman et al. |
| 2004/0204635 | A1 * | 10/2004 | Scharf et al. ............... 600/323 |

FOREIGN PATENT DOCUMENTS

| | | |
|---|---|---|
| DE | 10009882 | 10/2001 |
| DE | 20119965 | 4/2002 |
| EP | 0770349 | 5/1997 |
| EP | 1070479 | 1/2001 |
| EP | 0876790 | 2/2003 |
| GB | 2003276 | 3/1979 |
| WO | WO 96/01585 | 1/1996 |
| WO | WO99/04685 | 2/1999 |
| WO | WO 00/40145 | 7/2000 |
| WO | WO 01/15056 | 1/2001 |
| WO | WO 01/97686 | 12/2001 |
| WO | WO 03/050642 | 6/2003 |
| WO | WO 03/050643 | 6/2003 |
| WO | WO2004/047633 | 6/2004 |

OTHER PUBLICATIONS

Rhee et al, "Artifact_resistant Power-Efficient Design of Finger-Ring Plethysmographic Sensors", *IEEE Transactions On Biomedical Enginering*, 48(7):795-805, 2001.

Yang et al, "A Twenty-Four Hour Tele-Nursing System Using a Ring Sensor", *Proc. Of 1998 Int. Conf. On Robotics and Automation*, Leuven, Belgium, pp. 387-392, 1998.

Rhee et al, "The Ring Sensor: A New Ambulatory Wearable Sensor for Twenty-Four Hour Patient Monitoring", *Proceedings of the 20th Annual International Conference of the IEEE Engineering in Medicine and Biology Society*, Hong Kong, 1998.

Mascaro, SA, "Photoplethymograph Fingernail Sensors for Measuring Finger Forces Without Haptic Obstruction", *IEEE Transactions On Robotics and Automation*, 17(5):698-708, 2001.

Yang et al, "Cuff-less Continuous Monitoring of Beat-to-Beat Blood Pressure Using Sensor Fusion", available through http://web.mit.edu/zyi/www/pdf/IEEETRans2000.pdf as of Dec. 9, 2001.

Yang, et al, "Sensor Fusion for Noninvasive Continuous Monitoring of Pulsating Blood Pressure Based on an Arterial Hemodynamic Model", available through http://www.mit.edu/afs/athena.mit.edu/user/z/y/zyi/www/pdf/ASME99.pdf.

Zhang et al. "A Telemedical Multilevel Server Network System", Chinese Journal of Medical Instrumentation, 25(1): 30-33, 2001. In Chinese, Abstract in English.

* cited by examiner

FIG. 4

| STX | Len | Flag | Addr(msb) | Addr(mid) | Addr(lsb) | CMD | Data(0) | ... | Data(n) | CRC(msb) | CRC(lsb) | ETX |
|---|---|---|---|---|---|---|---|---|---|---|---|---|

STX   Start of TX indicates the beginning of the message ( 7E hex).

Len   indicates the number of data bytes that the message contains (0 to n + 2 bytes).

Len = 0 – No command.

Len = 1 – command only; the message not include data(0) through data(n)

Len >2 – the message includes command and data.

Flag   status bits (1 byte)

Addr   the user ID of the bracelet, 24 bits (0 to16777216).

CMD   command description.

Data(n)   the data of the message.

CRC   the CRC (2 bytes) for the message beginning from STX byte to Data(n) byte

ETX   End of TX indicates the end of the message ( 7B hex)

METHOD AND DEVICE FOR MEASURING PHYSIOLOGICAL PARAMETERS AT THE WRIST

CROSS-REFERENCE TO RELATED APPLICATION

This application is a National Phase Application of PCT/IL02/00995 having International Filing date of 10 Dec. 2002, which claims priority from U.S. patent application Ser. No. 10/006,357 filed Dec. 10, 2001 entitled, "Method and Device for Measuring Physiological Parameters at the Wrist," the subject matter of which is incorporated herein by reference.

FIELD OF THE INVENTION

The present invention is of a method and device for measuring at least one physiological parameter of a subject at the wrist, preferably for extracting clinically useful information thereof. More specifically, the present invention is of a device which may be worn at the wrist of the subject with a strap or other fastening article, and which may then be used to monitor the subject through measurement of the physiological parameter.

BACKGROUND OF THE INVENTION

Currently, a number of different types of devices are available for monitoring human subjects in a non-invasive manner. For example, heart function can be monitored in a user through the use of electrodes, which must be attached to the skin of the user. Although non-invasive, such equipment is nevertheless uncomfortable for the user, who is attached to a network of cables and wired sensors. In addition, such equipment is very expensive, limiting its use to hospitals and other medical settings in which both the cost and the discomfort of the patient can be justified. Furthermore, patients may become anxious when examined by medical personnel, thereby significantly altering the normal readings for these patients. It should be noted that the terms "subject", "patient" and "user" are used interchangeably herein.

However, there are many different situations in which non-invasive monitoring of a human subject is desired. For example, such monitoring could be very useful as part of the overall health maintenance of the human subject, and could be used in order to detect a deterioration in the physiological condition of the subject before a concomitant deterioration in the health of the subject becomes noticeable. Examples of adverse physiological conditions which could be detected with regular non-invasive monitoring include but are not limited to excessive weight gain or less; arrhythmia and other heart conditions; incipient diabetes in the form of improper glucose metabolism; and loss of lung capacity or other problems with respiration.

Heart rate and blood pressure are important factors in determining the state of a person's health and the physical condition of a person's body in response to physical or emotional stress. Periodic monitoring of these physical parameters is particularly important for individuals having cardiac disease and/or lowered cardiac functioning, or high blood pressure. However, physically healthy individuals may also wish to periodically monitor their heart rate and blood pressure in stressful situations, for example when engaging in strenuous exercise.

In order to support regular monitoring of human subjects in their normal environment, such as in the home and at the office for example, the equipment must be non-invasive and easy to use. The equipment would then be able to monitor at least one physiological parameter of the user, without requiring the user to perform any complicated actions and/or to operate complex devices. Indeed, it would be highly preferred for the equipment to be incorporated as part of the regular daily living routine of the subject, since the requirement for any additional or special actions on the part of human subject is likely to result in decreased compliance. In addition, the equipment should be robust yet inexpensive.

One example of such a device incorporates a wristband to attach a physiological sensor to the wrist of the subject. Currently, a number of different types of such wristband devices are available, most of which are intended to be used as stand-alone devices to provide information about the subject's own physical condition, mainly for heart rate and blood pressure. Most of these devices obtain such measurements by using an inflating cuff, which is bulky and awkward for the subject.

Wrist-mounted heart rate monitors are known to the art and have been disclosed, for example, in the patent to Orr et al, U.S. Pat. No. 3,807,388, wherein the duration of a heart beat is measured by counting electrical pulses recurring at a known frequency. The duration of the heartbeat is then related to a particular average heart beat rate. However, the disclosed measurement system does not directly measure the heart rate and, therefore, is subject to inaccuracies of measurement due to the instability of heart beat duration over brief intervals of time.

A blood pressure measuring device is disclosed in the patent to Petzke et al, U.S. Pat. No. 3,926,179, in which a probe is applied adjacent to the radial artery of a wrist. A pressure-sensitive transducer on the probe generates electrical signals corresponding to the blood pressure pulses of the radial artery. The electrical pulses are applied to analog circuitry that generates a systolic signal corresponding to the integrated voltage at the peak of the electrical pulse signal and a diastolic signal corresponding to the voltage at the low point of the pulse signal. The analog device of Petzke et al requires a substantial amount of power to operate and, therefore, is not suitable for use in a small, compact stand-alone device for being worn on the wrist.

A blood pressure and a heart rate measuring wrist watch is also disclosed in the patent to Broadwater, U.S. Pat. No. 4,331,154, in which a digital watch is employed to measure systolic and diastolic blood pressure as well as heart rate. The band of the watch supports a piezoelectric transducer that is held in contact with the wrist adjacent to the radial artery when a switch on the band is activated. The absolute values required for this method to evaluate blood pressure cause the device to be subject to inaccurate readings, since the tissues of the hand and wrist may be expected to expand and contract according to such factors as the time of day, and the condition of the external environment such as the atmospheric pressure. Such expansion or contraction may cause different degrees of tension on the wrist-mounted device, which is therefore not suitable for use without daily calibrations.

Other wrist-mounted devices are for wireless panic alarm systems, mainly for elderly people who live alone. These devices are usually shaped as a wristband or a pendant. Whenever the user becomes distressed, the user presses a panic button located on the device. The device then sends a digitally coded wireless message to a gateway device located nearby, usually in the same room, by using a unidirectional wireless data communication link. The gateway device then contacts a manually operated contact center, for example with a land based or cellular telephone connection. A particular identifier for the user is usually sent first, after which the human operator is allowed to talk to the user through a speaker and to listen through a sensitive microphone located within the gateway. However, none of the above systems contains any physiological measurement device within, in order to learn about the current physiological status of the user.

In such a situation as described above, the operator at the call center learns about the user's condition only by speaking with the user. However, this is only possible if the user is actually able to speak. High levels of background noise may also prevent the user from being heard by the microphone of the gateway device.

SUMMARY OF THE INVENTION

The background art does not teach or suggest a device which can conveniently, non-intrusively and autonomously measure one or more physiological parameters, in order to extract medical information such as heart rate, breathing rate and blood pressure, and which may be worn on the wrist of the user. The background art also does not teach or suggest such a wrist-mounted device, which can measure such parameters and then send the information to a contact center or other location containing medical personnel. The background art also does not teach or suggest such a wrist-mounted device which is compact, non-invasive, and light.

The present invention overcomes these deficiencies of the background art by providing a wrist-mounted device for measuring at least one physiological parameter of the user. The present invention enables such a measurement to preferably be transformed into medical information about the user, and/or displays the results on a LCD display. As used herein, the term "physiological parameter" refers to the signal which is received from the sensor, while the term "medical information" refers to the information which may be extracted or otherwise obtained by analyzing this signal and/or a combination of signals. Such information may then optionally be sent to medical personnel (for example at a contact monitoring center) and/or to a remote server, through a gateway device. The gateway device preferably communicates with the wrist-mounted device of the present invention through a wireless communication channel.

The present invention has the option to display the medical information to the user on a local LCD display, such that the user is optionally and preferably able to read the result locally. Examples of medical information which may be extracted from the measured physiological parameter or parameters include, but are not limited to: heart rate; regularity in heart rate; breathing rate; arrhythmia of the heart (if any), as well as the general rhythm and functioning of the heart; blood pressure; presence of abnormal body movements such as convulsions for example; body position; general body movements; body temperature; presence and level of sweat; oxygen saturation in the blood; and glucose levels in the blood.

In addition to the physiological parameters, the present invention may measure other parameters that may affect the subject's physical condition, including but not limited to ambient temperature and humidity, lighting conditions, smoke or other material in the air, distance from home etc.

Optionally and more preferably, the present invention also features an alarm signal for being transmitted through the gateway device in order to indicate an emergency or otherwise dangerous situation for the user. The alarm signal may optionally be transmitted according to a manual action of the user, such as pressing a "panic button" for example.

Upon receipt of the manually activated alarm signal, the gateway would preferably initiate immediately a call to a human operated call center. Then the device would preferably automatically collect one or more current measurements of physiological parameters of the user. These measurements may be sent directly to the gateway, or alternatively may be analyzed in order to compute the medical information of the user before sending the results to the gateway. The human operator would then preferably be able to assess the user's medical condition from the received information.

Most preferably, the alarm signal is transmitted automatically upon measurement of one or more physiological parameters of the user, even if the user is unable to press the panic button. Optionally, the alarm signal may be given to the user, additionally or alternatively, for example by sounding an audible alarm, more preferably from the wrist-mounted device itself.

The device of the present invention also monitors, at least periodically or continuously, one or more physiological parameters of the user. Continuous monitoring would more easily enable the device to transmit the alarm signal if one or more physiological parameters are determined to be outside of predefined criteria, which may represent such medical information as unstable or excessive heart rate, or very high or low blood pressure.

According to an exemplary embodiment of the present invention, the wrist-mounted device features one or more sensors attached to a wristband or other fastening article. The sensor(s) may optionally be connected to a microprocessor, optionally by a wire but alternatively through a wireless connection. The microprocessor may optionally also be located within the wristband, or otherwise attached to the wristband. The sensor(s) may optionally support automatic collection of the measurement of the at least one physiological parameter, while the microprocessor is able to execute one or more instructions for extracting medical information about the user from such measurement(s).

The microprocessor more preferably operates a software program to process and analyze the data which is collected, in order to compute medical information. The extracted information, optionally also with the raw data, is then preferably transferred to the previously described gateway device. The gateway device may optionally relay such information to a remote server, which more preferably is able to provide such information to medical personnel, for example as part of a contact center. Therefore, continuous monitoring of the medical information and/or physiological parameters of the user may optionally and more preferably be made, enabling better medical care for the user. According to the present invention there is provided a device for measuring at least one physiological parameter of a subject, comprising: (a) a fastening article for being fastened to a wrist of the user; (b) at least one sensor for measuring at least one physiological function of the user, the sensor may be in contact with at least a portion of the wrist and the sensor being attached to the fastening article; and (c) a processor for receiving a signal from the sensor and for converting at least one measurement to form the at least one physiological parameter. Optionally, the data may be stored on a non-volatile memory for being downloaded later by the user or by an operator.

According to another embodiment of the present invention, there is provided a system for measuring at least one physiological parameter of a subject, comprising: (a) a device for measuring the at least one physiological parameter, comprising: (i) a fastening article for being fastened to a wrist of the user; (ii) a sensor for measuring at least one physiological parameter of the user, the sensor being in contact with at least a portion of the wrist and the sensor being attached to the fastening article; (iii) a communication unit for at least transmitting data; and (b) a gateway device for receiving the transmitted data for being monitored.

According to another embodiment of the present invention, there is provided a method for monitoring a physiological parameter of a user, comprising: providing a device for monitoring the physiological parameter, the device being attached to at least a portion of the user at a pulse point of the user; monitoring the physiological parameter through the pulse point; and if a level of the physiological parameter of the user is outside of an expected range, transmitting an alarm.

According to still another embodiment of the present invention, there is provided a device for measuring at least one physiological parameter of a subject, comprising: (a) a fastening article for being fastened to a wrist of the user; (b) a piezoceramic sensor for measuring at least one physiological parameter of the user at a pulse point of the wrist and the sensor being attached to the fastening article; and (c) a processor for receiving a signal from the sensor and for converting the at least one measurement to form medical information.

Hereinafter, the term "microprocessor" includes, but is not limited to, general-purpose microprocessor, a DSP, a microcontroller or a special ASIC designed for that purpose.

The method of the present invention could be described as a process for being performed by a data processor, and as such could optionally be implemented as software, hardware or firmware, or a combination thereof. For the present invention, a software application could be written in substantially any suitable programming language, which could easily be selected by one of ordinary skill in the art. The programming language chosen should be compatible with the computational device (computer hardware and operating system) according to which the software application is executed. Examples of suitable programming languages include, but are not limited to, Visual Basic, Assembler, Visual C, standard C, C++ and Java.

BRIEF DESCRIPTION OF THE DRAWINGS

The invention is herein described, by way of example only, with reference to the accompanying drawings, wherein:

FIG. 4 describes a bi-directional message format between the device and the gateway;

DESCRIPTION OF THE EXEMPLARY EMBODIMENTS

Figure 1:
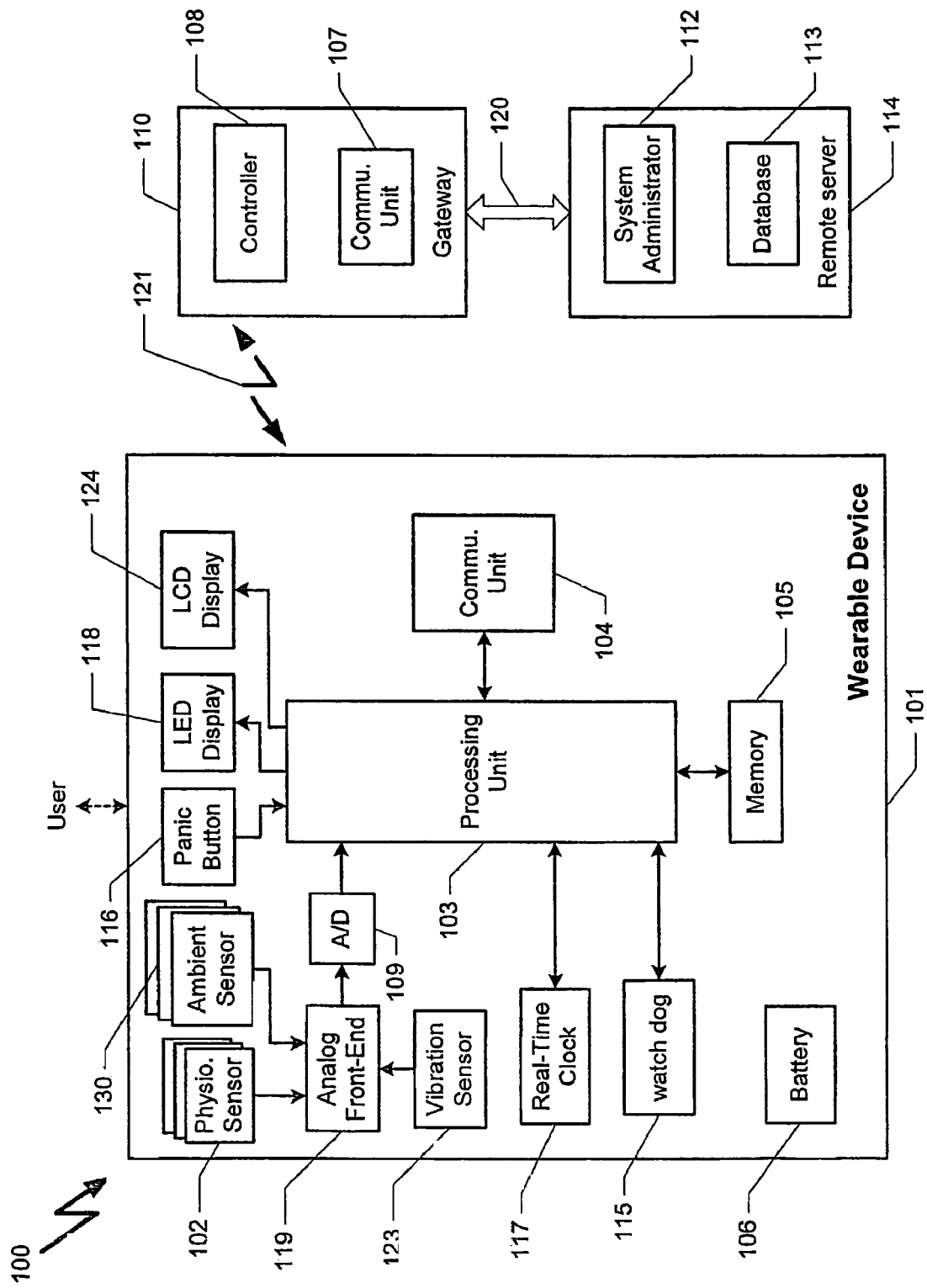
FIG. 1 is a schematic block diagram of a system according to an exemplary embodiment of the present invention.

The present invention is of a wrist-mounted device for measuring at least one physiological parameter of the user. The present invention enables such a measurement to preferably be transformed into medical information about the user. Such information may then optionally be sent to medical personnel (for example at a contact monitoring center) and/or to a remote server, through a gateway device. The gateway device preferably communicates with the wrist-mounted device of the present invention through a wireless communication channel.

Examples of medical information which may be extracted from the measured physiological parameter or parameters include, but are not limited to: heart rate; regularity in heart rate; breathing rate; arrhythmia of the heart (if any), as well as the general rhythm and functioning of the heart; blood pressure; presence of abnormal body movements such as convulsions for example; body position; general body movements; body temperature; presence and level of sweat; oxygen saturation in the blood; and glucose levels in the blood.

Optionally and more preferably, the present invention also features an alarm signal for being transmitted through the gateway device in order to indicate an emergency or otherwise dangerous situation for the user. The alarm signal may optionally be transmitted according to a manual action of the user, such as pressing a "panic button" for example.

Most preferably, the alarm signal is transmitted automatically upon measurement of the one or more physiological parameters of the user, preferably even if the user is unable to press the panic button. Optionally, the alarm signal may be given to the user, additionally or alternatively, for example by sounding an audible alarm, more preferably from the wrist-mounted device itself.

An exemplary embodiment of the present invention may measure also parameters that may affect the subject's physical condition, including but not limited to ambient temperature and humidity, lighting conditions, smoke and/or other material in the air, distance from home etc.

Upon receipt of the manually/automatically activated alarm signal, the gateway would preferably initiate immediately a call to a human operated call center. Then the device would preferably automatically collect one or more current physiological measurements of the user. These measurements may be sent directly to the gateway, or alternatively may be analyzed in order to compute the medical parameters of the user before sending the results to the gateway. The gateway may also analyze the measurement, for example when the measurements are transferred directly to the gateway. The human operator, at the medical center, would then preferably be able to assess the user's medical condition from the received information. It should be noted that the terms "medical center" and "call center" are used interchangeably herein.

The device of the present invention may also monitor, at least periodically but more preferably continuously, the value or condition of one or more physiological parameters of the user. Continuous monitoring would more easily enable the device to transmit the alarm signal if measurements of one or more physiological parameters are collected and analyzed by the microprocessor to form medical information, which then could be determined to be above predefined criteria, such as unstable heart rate, or very high or low blood pressure, for example.

According to a non-limiting exemplary embodiment of the present invention, the wrist-mounted device features one or more sensors attached to a wristband or other fastening article. The sensor(s) are preferably connected to a microprocessor, optionally by a wire but alternatively through a wireless connection. The microprocessor may optionally also be located within the wristband, or otherwise attached to the wristband. The sensor(s) preferably support automatic collection of at least one physiological measurement; more preferably, the microprocessor is able to execute one or more instructions for extracting clinically useful information about the user from such measurement(s).

The microprocessor more preferably operates a software program to process and analyze the data which is collected, in order to compute medical information. The extracted medical information, optionally also with the raw data, is then preferably transferred to the previously described gateway device. The gateway device then preferably relays such information to a remote server, which more preferably is able to provide such information to medical personnel, for example as part of a contact center. Therefore, continuous monitoring of the physiological parameters of the user may optionally and more preferably be made, enabling better medical care for the user.

A general, non-limiting example of suitable methods for measuring the heart rate and/or other heart-related physiological parameters of a subject who is wearing the device according to the present invention may be found in the article "Cuff-less Continuous Monitoring of Beat-To-Beat Blood Pressure Using Sensor Fusion", by Boo-Ho Yang, Yi Zhang and H. Harry Asada—IEEE (also available through http://web.mit.edu/zyi/www/pdf/IEEETrans2000.pdf as of Dec. 9, 2001), hereby incorporated by reference as if fully set forth herein, where systolic and diastolic blood pressure are calculated using the pulse pressure shape per heartbeat. The disclosure does not describe a device which has the functionality according to the present invention, but the disclosed method is generally useful for determining blood pressure from an external measurement of pressure from the pulse through the skin of the subject.

The principles and operation of a device and method according to the present invention may be better understood with reference to the drawings and the accompanying description.

Referring now to the drawings, FIG. 1 is a schematic block diagram of a system according to the present invention. As shown, a system 100 features a wearable device 101 to be worn by a user, preferably as a wrist-mounted device, for example by being attached with a wristband or other fastening article to the wrist of the user. Device 101 features at least one physiological sensor 102 for measuring at least one physiological parameter of the user. The function of an exemplary sensor 102 is described in greater detail below.

The device 101 may optionally feature a vibration sensor 123, preferably a piezoceramic sensor, which is not in direct contact with the skin of the user. Sensor 123 measures the movement of the wrist. The output of sensor 123 can be used by a processing unit 103 to capture the movement of the wrist and to recover some noise received by sensor 102, which is caused by such movement.

Device 101 may include additional ambient sensors 130 or additional measuring routines for measuring other parameters. For example, device 101 may optionally have a humidity sensor for measuring the ambient humidity. An exemplary humidity sensor may be the Humidity Gauge manufactured by Honeywell.

In order to support processing of the measured physiological parameter or parameters, processing unit 103 may optionally include internal RAM and non-volatile program memory (not shown). Also processing unit 103 may optionally include an extended data memory 105 located externally to processing unit 103. Processing unit 103 preferably executes at least one instruction for processing the data obtained by sensor 102.

Examples of such processing units 103 include but are not limited to PIC18LC452 by Microchip Technology Inc., which contains 10 channels of 10 bit A/D converters, a 1.5K bytes of internal RAM and 32K Bytes of non-volatile program memory.

Extended memory component 105 is preferably an electrically erasable non-volatile external memory component. Examples of such a memory component include but are not limited to FM24CL64-S (Ramtron, USA), with 64 Kbit of fast access read/write serial memory for storing temporary data related to the sampled physiological parameter.

Device 101 may optionally feature a real time clock 117 in order to provide an accurate time and date for each measurement, as device 101 can optionally store a few measurements before transmitting such data and/or information to a gateway device 110, as described in greater detail below. Stored data and/or information may also optionally be used for such applications as reminding the subject to take medication, perform a prescheduled measurement, and so forth. An A/D converter 109 with multiple inputs is also optionally and preferably present if sensor 102 is an analog sensor, in order to convert the analog signal to a digital signal.

Device 101 preferably features an internal communication unit 104, for at least unidirectional, but more preferably bi-directional, communication with gateway device 110. Gateway device 110 may feature a communication unit 107. Communication unit 104 may optionally communicate with communication unit 107 through a wire or alternatively through a wireless communication link 121. According to a non-limiting exemplary embodiment of the present invention, gateway device 110 is located relatively close to the user and hence to device 101, for example by being located at the user's premises. As a non-limiting example, gateway device 110 could optionally be installed in the home of the user.

Gateway device 110 also optionally and preferably features a controller 108 for controlling functions of gateway device 110, such as communication with device 101 for example.

Gateway device 110 preferably communicates with a remote server 114 through a data link 120, which could optionally be a direct dial-up modem connection with DTMF coding or TCP/IP using regular LAN or dial-up modem connection to an ISP, for example. In any case, data link 120 may optionally be a wired or wireless link, for example through a cellular telephone and/or land-based telephone system, or a combination thereof.

Remote server 114 may be controlled by a system administrator 112, which may be a person (for manual operation) or a software program (for automatic operation), or a combination thereof. Remote server 114 also preferably features a database 113 for storing data received from gateway device 110.

Device 101 may also feature a manually operated panic alarm button 116 to be manually activated by the user, for example if the user is in distress. Device 101 may also optionally feature a LED display 118, for example in order to indicate of alert activation or a low battery level.

Physiological sensor 102 is preferably part of a sensor assembly. Without the intention to limit in any way, the following discussion centers on such a physiological sensor 102, which contains a piezoceramic transducer for generating an electrical signal, having amplitude corresponding to the magnitude of applied pressure. Therefore, if at least a portion of the transducer is located adjacent to, and in physical contact with, an area of the wrist where blood pressure pulses may be detected, the transducer generates electrical pressure pulses corresponding to the detected blood pressure pulses. Each of the electrical pressure pulses preferably defines a maximum voltage over a systolic interval and a minimum voltage over a diastolic interval.

Although a piezoceramic sensor is used as a pressure transducer according to a preferred embodiment of the invention, it should be appreciated that other transducers known to the art may be employed without departing from the spirit of the invention. Examples of such sensors include but are not limited to piezoelectric transducers, resistive strain gauges and pressure sensor made of fiber-optic techniques.

The piezoceramic transducer is desirable for the present invention since the transducer measures the direct effect of the pressure exerted within the radial artery, while other transducers, for example resistive strain gauges, measure secondary effects such as the strain forces that are applied at the surface of the skin due to the expansion of the radial artery. Piezoceramic transducers are also cheaper than piezoelectric transducers but still produce a high-quality signal.

As shown with regard to FIG. 1, the analog output of sensor 102 is first preferably treated by an analog front-end 119, which more preferably contains analog selector to select the appropriate sensor followed by an analog filter (not shown). As a non-limiting example, this analog filter preferably has a cutoff of about 20 Hz, a linear phase response, a flat amplitude response up to 10 Hz and an amplification of about 3 for acquiring the full spectrum of a typical blood pressure pulse. The filtered signal then enters A/D converter 109.

Processing unit 103 preferably controls the operation of A/D converter 109. When a physiological measurement is initiated, A/D converter 109 starts sampling the filtered analog signal of sensor 102 from analog front-end 119, preferably at a rate controlled by processing unit 103. This rate is optionally and more preferably 80 samples pet second as to over sample the data by a factor of 4 to maintain a good quality sampled signal. A/D converter 109 preferably transfers the analog data into a digital coded word, optionally at resolution of 10 bits per sample, for example.

An exemplary measuring period may be about 30 seconds in which data is gathered at processing unit 103. Processing unit 103 preferably operates a software program for examining the validity of the sampled data, in order to determine whether the data contains some indications of legitimate physiological data (such as of a blood pressure pulse of an artery) or alternatively whether the data contains only noise or poor readings. In the second case, A/D converter 109 preferably starts sampling the signal again in order to obtain data for measurement. This process preferably continues until the software determines that sufficient valid data has been collected or after a few successive rejections (usually after 3 times).

Then, the software program preferably performs an algorithm for calculating some medical parameters from the sampled data, such as the calculation of systolic and diastolic blood pressure using a method as disclosed in U.S. Pat. No. 4,418,700, which is hereby incorporated by reference as if fully set forth herein.

The calculated parameters are then preferably stored in memory 105. The data stored in memory 105 is preferably transmitted to gateway device 110 periodically, or alternatively or additionally after manual operation of panic button 116.

The calculated parameters are also optionally and preferably displayed on a local LCD display 124, so the user can view the last medical results locally.

More preferably, data for all medical parameters that are sent to remote server 114 are sent according to a security protocol for maintaining the privacy of the user.

Furthermore, the software program preferably performs another algorithm for generating an alert if the medical parameters have values beyond or otherwise outside of the normal expected values.

Although a one-way link from device 101 to gateway device 110 may be used, device 101 preferably features a two-way communication link as shown for link 121, for establishing more reliable communication with gateway device 110. Examples of communication units 104, 107 include but are not limited to an RF401 UHF transceiver (Nordic), which operates in the universal ISM band (433.92 Mhz), an infrared transceiver, and a "Bluetooth" protocol enabled-transceiver operating bi-directionally in the 2.4 GHz band.

Device 101 preferably has its own unique identifier, stored in non-volatile data storage, more preferably in memory 105. Each time device 101 sends a wireless message to gateway device 110, device 101 also preferably sends the unique identifier to gateway device 110, although optionally the identifier may be sent only periodically, for example once per day. Gateway device 110 also preferably sends a message to a particular device 101 by including the device identifier in the message, thereby specifying which such device should receive the message.

As previously described device 101 preferably has its own real time clock 117. For periodic monitoring of the user, real time clock 117 is preferably used to provide a time tag for each set of results. This time tag is very important for continuous monitoring of the user for long periods of time. By examining the data recorded over of the user for long period of time, a change or alteration in the health condition of the user may be detected. Real time clock 117 may optionally be implemented by separate hardware such as RTC8564 (EPSON, US) for example, or alternatively by a software program for operation by processing unit 103.

In some embodiments of device 101 the output of real time clock 117 may be displayed on one of displays 118 or 124 for displaying the date and time.

Device 101 may also optionally feature a watchdog 115, which monitors the function of device 101. If the end of a watchdog time period is reached, device 101 is assumed to have a fault in its operation, and a master reset is preferably initiated automatically.

Device 101 also preferably features a power source such as a battery 106, which powers device 101. Examples of suitable batteries include but are not limited to the silver oxide coin battery model 386 (Panasonic, Japan) having 150 mAh in capacity with a pulse burst of 75 mA for a short period of time (about 5 sec for each pulse). Battery 106 optionally and preferably contains enough energy to power the device for more than one year of operation without being replaced.

Figure 2:
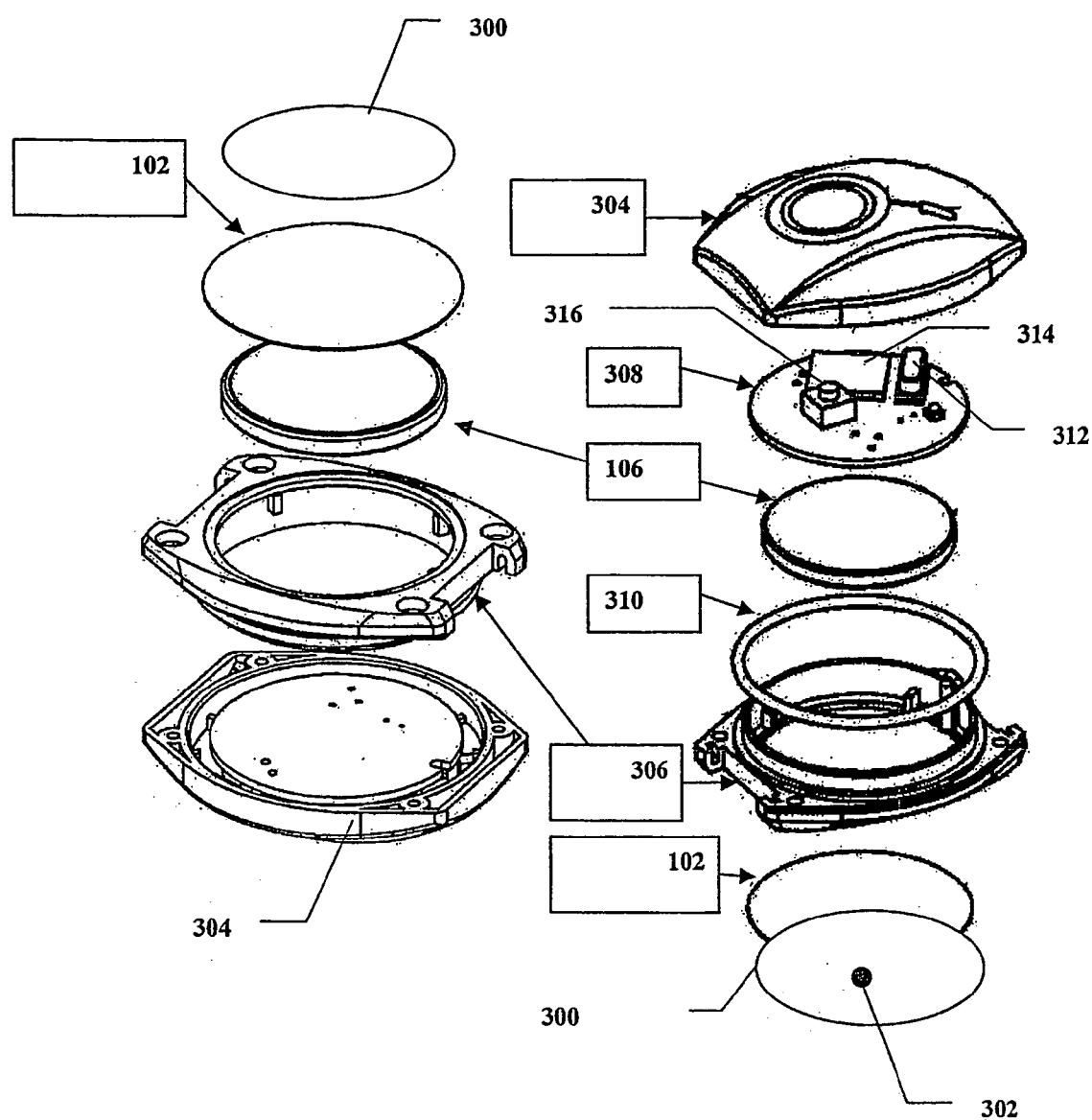
FIG. 2 shows an exploded view of an exemplary device.

FIG. 2 shows an exploded view of an exemplary device according to FIG. 1. As shown, the device features sensor 102, shown with the preferred but exemplary implementation of a piezoceramic sensor as previously described. The device also optionally and preferably features battery 106, and a push button 316 (for optional implementation of the panic button of the device of FIG. 1). Battery 106 may optionally be replaced with a plurality of smaller batteries (not shown). The device preferably features a processor 314 (which may optionally be similar or identical to the processing unit of the device of FIG. 1. The components of the device are preferably held by a case 306.

For this exemplary implementation, sensor 102 is in physical contact with an anvil 300 via a protrusion 302. Protrusion 302 is welded, optionally by a laser, on one side to the center of anvil 300 and on the other side to the center of sensor 102. Anvil 300 is pressed against the skin of the wrist of the subject (not shown), more preferably at a pulse point. Anvil 300 may optionally be a rigid disk made for example of polymer, or optionally a metal, such as gold plated copper or stainless steel, for example. Of course, any other type of suitable material, or combinations of materials, may also optionally be used. Anvil 300 therefore collects and integrates the pressure waves, which are associated with each pulse of the blood of the subject, from the area below anvil 300. This pressure is preferably transferred from the center of anvil 300 to the center of sensor 102 via protrusion 302. Sensor 102 then emits voltage to form a signal, preferably according to a linear output. By using this architecture, the present invention may measure the blood pressure pulse without blocking the blood flow in the artery.

This signal is then received by processor 314, which preferably extracts medical information from the measurement of the physiological parameter. Processor 314 optionally and preferably features a crystal oscillator 312, for stabilizing the internal clock of processor 314. Processor 314 may communicate with the real time clock of the device (not shown). Also not shown are the extended memory, transceiver (communication unit), A/D converter and analog front end of the device.

Processor 314, oscillator 312 and push button 316 are all preferably mounted on a PCB board 308. PCB board 308 is then preferably sandwiched between battery 106 and a device cover 304. Device cover 304 preferably features a soft portion, which may be rubber for example, for enabling the user to locate and depress the panic push button through push button 316.

An o-ring 310 is preferably used for waterproof sealing between cover 304 and the: case 306 of the device. Anvil 300 then is held between sensor 102 and the skin of the user (not shown), for example.

According to an alternative implementation of the device of FIGS. 1 and 2, sensor 102 and anvil 300 could optionally be located in the wristband for affixing the device to the wrist of the user (not shown).

Figure 3:
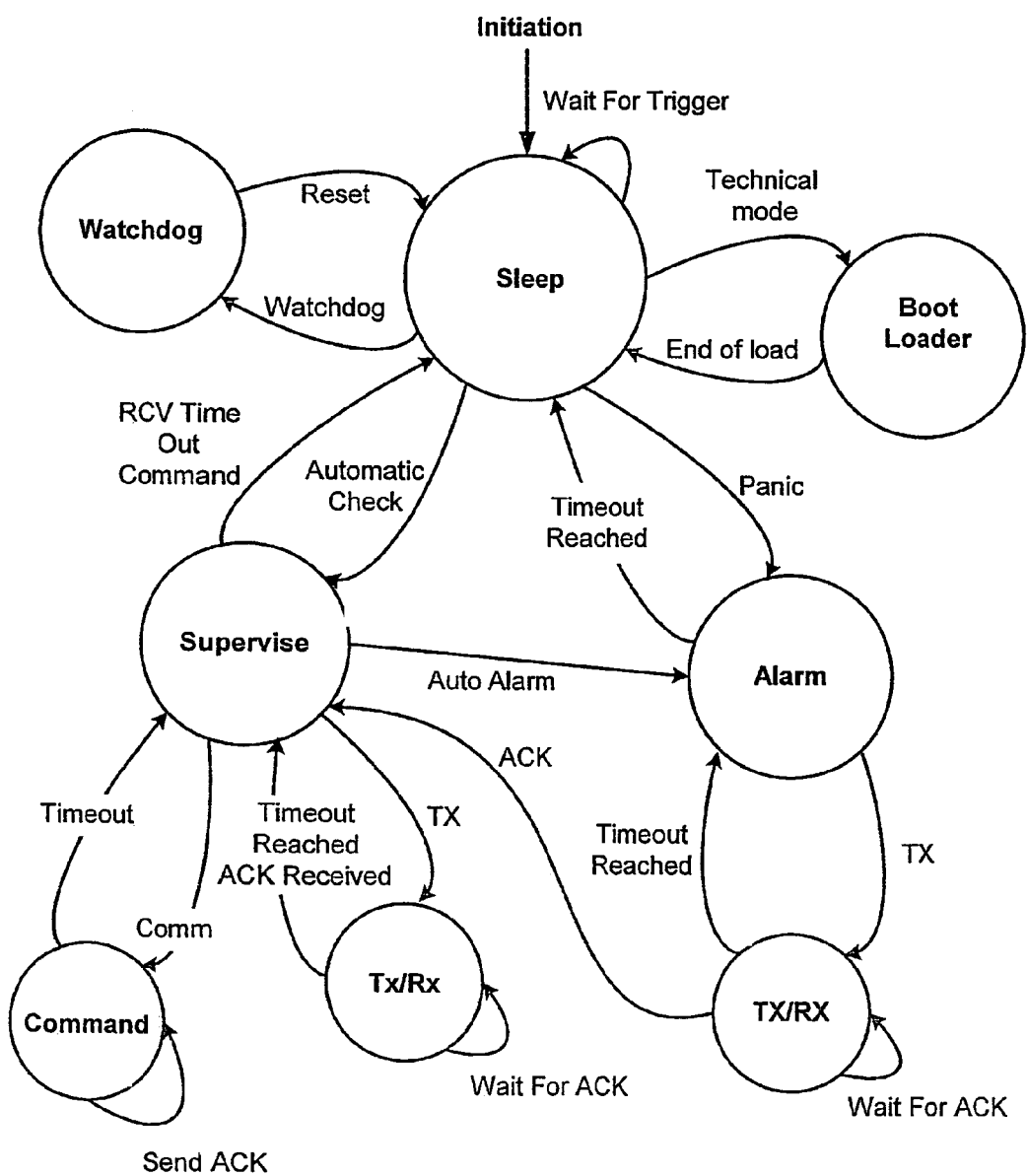
FIG. 3 describes a general state flow diagram.

FIG. 3 is a state flow chart of the operation of the device. As the device software begins operation for the first time, the software preferably makes some initializations using default values. Once the device has been initialized, the software preferably triggers a watchdog function shown as a "Watchdog" process, and then enters a sleeping mode for saving battery life, shown as a "Sleep" process.

If the end of a watchdog time period is reached, the device is assumed to have a fault in its operation, and a master reset is preferably initiated automatically.

The device is preferably "woken up" according to one of three triggers. First, the device is preferably woken up when the user presses a panic button manually. This process is shown by the "Alarm" state. The device then preferably immediately starts a transmission to the gateway device, containing a distress indication and the device identifier. Then the device enters a receiving mode for a few seconds, waiting for acknowledge (ACK) from the gateway device. This process is shown as a "TX/RX" state.

If the acknowledge message is not received within this period of time a repeated message is initiated. Additional transmissions are initiated, if necessary. However, if after a predefined number of repeated times an acknowledge message is not received, an error message is stored within a log and no more tries are made. More preferably an indication LED starts blinking for a few seconds, optionally with an audible alarm. Then, the process returns to the "Sleep" state.

After receiving acknowledge, the process turns to "Supervise" state, where the device collects data from its sensors, preferably calculates some medical information concerning the current physiological status of the user. Then, the device turns into "Tx/Rx" state, where the device transmits a message containing the identifier, and the calculated medical parameters. And if the received ACK contains no commands the device returns to the "Sleep" state, otherwise the device does the command and sends an ACK to the gateway. The gateway returns an ACK with another command to continue or without a command to terminate this process. After doing the last command the device returns to the "Sleep" state.

In the next case where the device exits its "Sleep" state, an external real time clock signals the device to execute an automatic check. Then, the process enters "Supervise" state as discussed in the above paragraph, only that this time for saving battery life, the device initiate the "Tx/Rx" process only once for a few successive times sending all the accumulated data in one transmission. Then, the device preferably enters a "Sleep" state unless the measured parameters exceed a predefined threshold at least once, but preferably for a few successive measurements. In this case, the device initiates an automatic alarm entering the "Alarm" state, if the device has permission to do so, as previously described.

When a timer for a supervise process has been running or after an alarm, the device preferably exercises an automatic check as described above, and after that initiates a transmission to the gateway device including all the data collected after the last transmission. Then the device preferably waits for acknowledge, preferably repeating the transmission again if not receiving such an acknowledge message. In the acknowledge message, a command for the device can be stored. In such a case the device performs this command and then the device sends an acknowledge message to the gateway device. This process may optionally continue until an acknowledge message without a command is received, after which the device preferably returns to sleep mode.

In the third case, the device exit "Sleep" mode if of technical reasons a technician wants to change the operation software, the device enters "Boot Loader" state where a new software is loaded "on the fly" without a need to disconnect the batteries.

Other exemplary embodiment may use additional routines and modes, such as a mode ihat verifies whether the user is in the user's premises for example. This mode is optionally initiated every few minutes and transmit acknowledge to the gateway. The gateway waits for those signals and if in a certain window of time, for example 30 minutes, an acknowledgment has not been received, the gateway calls the medical center and reports that the user is missing.

FIG. 4 describes an exemplary message format for exchanging messages between the device and the gateway device. Every message preferably starts with a preamble STX byte (hex 7E), followed by a byte which contains the number of bytes in the current message, and three bytes of address, followed by a command byte and its corresponding data bytes. This is followed by two bytes of CRC and an ETX byte (hex 7B).

As such, the message is a variable length message with strong error detection and correction method for enhanced communication reliability. Each message optionally and preferably contains a low battery indication, if necessary.

In case of a unidirectional communication link between the device and the gateway, a repeated message is preferably transmitted for a predefined number of times, such as 20 times for example, after which the device preferably enters a sleeping mode if no answer is received.

In case of a bi-directional link, for each message sent to the gateway device, an acknowledge message is preferably returned by the gateway device and vise versa. This message may also contain a command for the device encoded in the CMD byte within the message. Commands could optionally include, but are not limited to, one or more of the following:

1) Get/Set service type
2) Get/Set device ID
3) Set interval between successive medical checking
4) Set interval between successive supervision transmissions
5) Set Time and date 6) Set threshold for automatic alerts
7) Set device calibration Each time the device sends a message to the gateway, the device may optionally contain a Battery OK/Battery Low indication for the battery situation. This signal preferably appears three months before the battery finishes, enough time to ask the user to replace the battery.

Each time the device sends a supervise-type message to the gateway, the device preferably sends also all the medical data stored in its memory with that message.

Each time the gateway device sends a command back to the device, the device preferably returns an acknowledge message with a 3 bit message serial number to the gateway device, in order to fulfill a full handshake between the two. If the gateway device does not receive acknowledge from the device within a few seconds, the gateway device preferably sends its transmission message again with the same serial number. The message may even be repeated a few times, each time waiting for acknowledge. If acknowledge is not received, a logbook is updated with an error message, and more preferably an indication LED is turned on for error indication.

Figure 5:
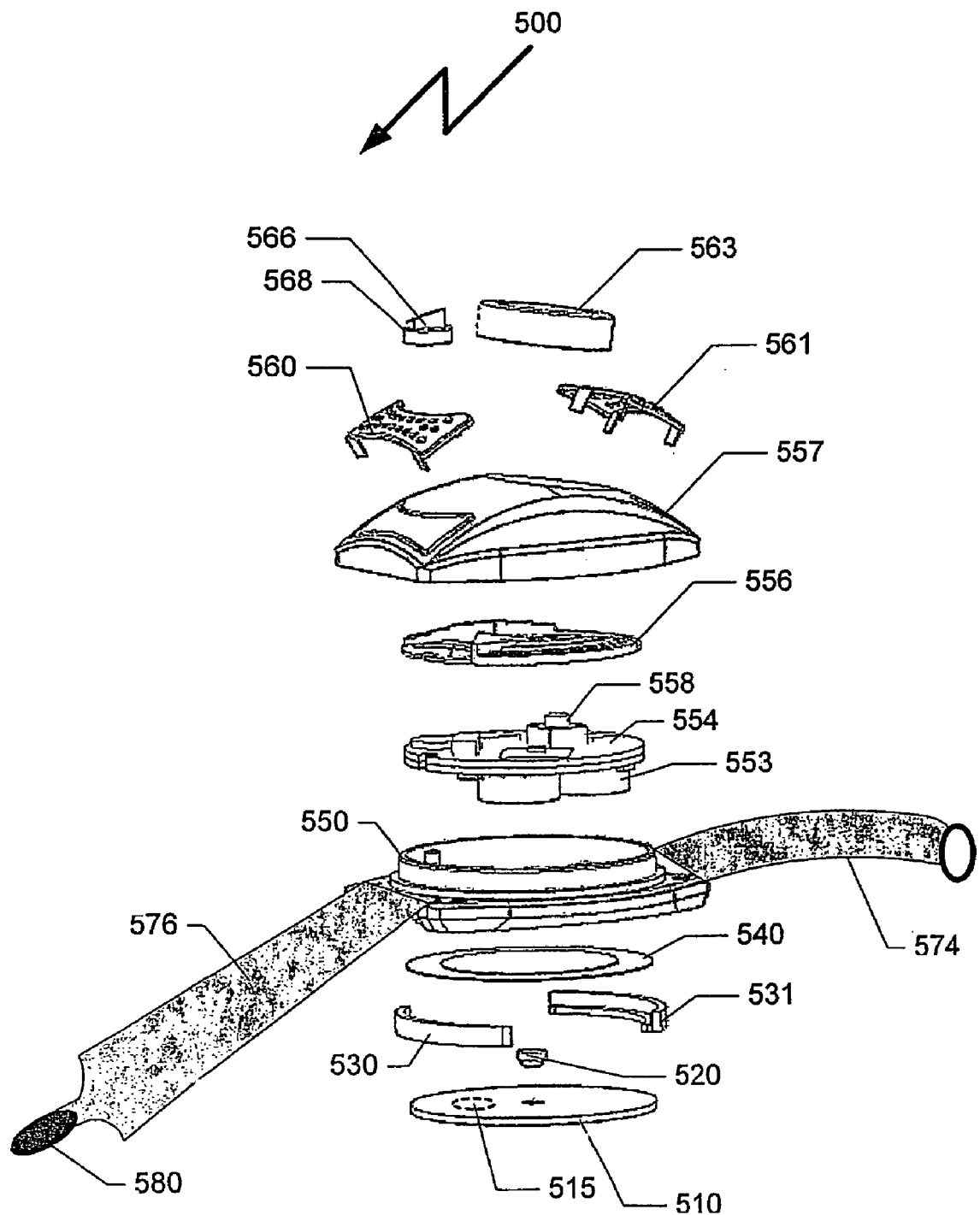
FIG. 5 shows an exploded view of an exemplary device with ECG option.

FIG. 5 shows an exploded view of a device 500 according to exemplary embodiments of the present invention. In addition to, or in place of, measuring blood pressure, device 500 may optionally measure other activities of the body including but not limited to ECG, tonus activity, temperature and the SpO2 (oxygen saturation in the blood) value in the blood of the user, for example.

Device 500 in FIG. 5 may be similar to an expanded wristwatch in shape, where bottom anvil 510 is the section which lies flat against the wrist. This forms the base of device 500 whose center is lower case 550. All other components are built onto lower case 550, culminating at the top with faceplate 557, upon which are mounted a number of additional components including sensors.

Sensor 540 is optionally and preferably attached to lower case 550 of device 500 by two arcs 530 and 531. Each arc 530 and 531 preferably has a vertical portion and a horizontal portion. The horizontal portion is preferably placed between sensor 540 and anvil 510, and is pressed against lower case 550 holding sensor 540 in place. The vertical portions of arcs 530 and 531 are preferably affixed into an appropriate slot in lower case 550 of device 500.

Lower case 550 may optionally have one or more electrical boards 554 and 556 that comprise the electrical circuitry, which is disclosed in conjunction to in FIG. 1 and or FIG. 5, of the device including batteries 553. A vibration sensor (an accelerometer) may optionally be connected to one of boards 554 or 556.

Device 500 is preferably covered by a top cover 557, that optionally and more preferably has two electrodes 560 and 561, SpO2 sensor 566 and optionally a single push panic button 558 that is preferably pressed by the user upon commencement of a measurement period, or if the wearer presses panic button 558.

Pressing the flexible portion 563 within top cover 557 causes panic button 558 to be pushed, and preferably initiates an automatic process within device 500. Device 500 preferably checks with gateway 110 (see FIG. 1) as to whether the user is already in a conference with the call center. If device 500 is found to be in a conference with the center, then device 500 may optionally start a measuring thread. If the user is not in conference with the call center, then device 500 preferably initiates the panic thread. The panic thread starts by establishing a connection with the call center via gateway 110 (FIG. 1). In parallel, device 500 preferably initiates the measuring thread and transmits a set of results to gateway 110. Gateway 110 optionally and preferably stores those results and upon establishing the connection with the call center, gateway 110 transmits the results to the call center.

In other embodiments, the panic thread starts upon pressing activation push button 558 for long period of time (e.g. above few seconds, 5, 6 etc.), thereby initiating a call to medical center. In contrast, pressing activation push button 558 for a short period of time, for example shorter than a second, starts an automatic measuring thread. It should be noted that the terms "activation push button", "panic push button", "panic button" or "push button" may be used interchangeably herein.

The measuring thread optionally and preferably starts by scanning the available sensors 102 for a first sensor 102 that produces a valid signal (see FIG. 1). A valid signal is defined as a signal that meets predefined requirements including but not limited to, one or more of the signal amplitude being within a certain range, frequency being within a certain range and so forth. The valid signal is processed by the appropriate analog front-end 119 and processing unit 103 (see FIG. 1). The medical information is preferably transferred to gateway 110, after which device 500 enters into Sleeping mode.

Upon receiving the awakening signal from a timer within the real time clock, device 500 may inform the user that a measuring process is initiated. Upon terminating the measurements, the results are sent to the remote server 114 (FIG. 1) via gateway 110.

Two bands 574 and 576 are optionally connected to lower case 550 and are preferably used to fasten the device to the wrist of the user. The long band 576 may optionally have a flexible conductive wire (not shown) which functions as an antenna, and which is connected to the transmitter of the communication unit 104, inside device 500, while the far end of long band 576 may comprise temperature sensor 580 connected by pair of wires (not shown) to the internal circuitry, both of which are described in greater detail below.

Device 500 may optionally be used to measure blood pressure pulse using piezoceramic transducer 540 to generate an electrical signal. The amplitude of the electrical signal from piezoceramic transducer 540 corresponds to the magnitude of pressure applied thereto. Piezoceramic transducer 540 may be a common piezoceramic buzzer, made of PZT material, and may optionally and additionally be used as a common buzzer, which receives the alarm signals from processing unit 103 (see FIG. 1) and produces the alarm sound. The alarm sound is generated by forcing voltage over piezoceramic transducer 540, which then buzzes for the duration of the alarm signal.

The exemplary sensor for sensing blood pressure pulse preferably comprises three elements: anvil 510, protrusion 520 and piezoceramic transducer 540. Protrusion 520 is preferably welded, optionally by a laser, on one side to the center of anvil 510 and on the other side to the center of piezoceramic transducer 540. Anvil 510 is pressed against the skin of the wrist of the subject (not shown), more preferably at a pulse point. Anvil 510 may optionally be a rigid disk or other structure, made for example of polymer, or optionally a metal, such as gold plated copper or stainless steel, for example. Of course, any other type of suitable material, or combinations of materials, may also optionally be used.

Anvil 510 therefore collects and integrates the pressure waves, which are associated with each pulse of the blood of the subject, from the area of skin below anvil 510. This pressure is preferably transferred from the center of anvil 510 to the center of piezoceramic transducer 540 via protrusion 520. Piezoceramic transducer 540 then emits voltage to form a signal, preferably according to a linear output. Protrusion 520 preferably is able to focus the input pressure, therefore increasing the output signal of piezoceramic transducer 540.

Therefore, if at least a portion of anvil 510 is located adjacent to, and in physical contact with, an area of the wrist where blood pressure pulses may be detected transducer 540 generates electrical pulses corresponding to the detected blood pressure pulses. Each of the electrical pressure pulses preferably defines a maximum voltage over a systolic interval and a minimum voltage over a diastolic interval. The electrical signal from transducer 540 is preferably amplified by analog front end 119 and transferred via A/D converter 109 to processing unit 103 (see FIG. 1). Processing unit 103 processes the digital signal and may deliver a plurality of medical information based on the measurement of blood pressure pulse including but not limited to heart rate, regularity in heart rate, breathing rate, arrhythmia of the heart (if any), general rhythm and functioning of the heart as well as the blood pressure amongst others.

Device 500 optionally and preferably features two conductive areas 560 and 561 at the top. In the bottom part of device 500, anvil 510 preferably has a conductive area 515, which preferably sits adjacent to the skin of the user. In some exemplary embodiments, conductive area 515 may cover the whole of anvil 510, a non-limiting example of which is constructing anvil 510 of metal. Each of conductive areas 560, 561 and 515 is preferably electronically connected, as one of the sensors 102, to an analog front-end 119 (FIG. 1).

Conductive areas 560, 561 and 515 may optionally and preferably be made of metal, polymer coated with a conductive layer or any other conductive material including but not limited to gold plated copper. Conductive areas 560, 561 and 515 form three electrodes that may be used for measuring electrochemical activity of the user's body (e.g. ECG, or tonus activity). This activity measures the effects of electricity on chemical and biological activities in the body, and is referred to hereinafter as electrochemical activity.

For optionally measuring ECG, the user has to touch, simultaneously, the two conductive areas 560 and 561 with the user's second hand, for example with two fingers, to form three measuring points including the skin portion, on the first hand, that is adjacent to conductive area 515. The three electronic signals from conductive areas 560, 561 and 515, are transferred to analog front-end 119 (FIG. 1). Analog front-end 119 extracts the ECG analog signal from the three signals by using the signal of one electrode as a reference and amplifying the differential voltage between the other two electrodes. The ECG analog signal is then transferred to A/D converter 109 and from there the digital ECG signal is transferred to processing unit 103 (FIG. 1). Analyzing the analog signal to extract the ECG signal may be done by electrical circuits that are known in the art.

Additional medical information may be determined from the ECG signal. For example, information about breathing rate may be processed based on methods that are described in the prior art. An exemplary method is disclosed in the following article: "Derivation of Respiration Signals from Multi lead ECGs". By George B. Moody, Roger G. Mark, Andrea Zoccola and Sara Mantero. This article originally appeared in Computers in Cardiology 1985, vol. 12 pp. 113-116 (Washington, D.C.: IEEE Computer Society Press), which is hereby incorporated by reference as if fully set forth herein.

Other medical information that may be produced by processor unit 103 (FIG. 1) is the Pulse Wave Transit Time (PWTT), that may be determined by measuring the time delay between the electrical pulse of the heart, measured from the ECG signal and the time of the blood pressure pulse.

In another exemplary embodiment, A/D converter 109 (see FIG. 1) may be integrated into processing unit 103. Processing unit 103 processes the ECG signal and generates medical information such as, but not limited to, heart rate, regularity in heart rate, breathing rate, arrhythmia of the heart (if any), as well as the general rhythm and functioning of the heart for example. The medical information is then transferred to the call center via gateway 110 (FIG. 1).

Device 500 may optionally be used for measuring the oxygen saturation in the blood (SpO2) by using SpO2 sensor 566. Sensor 566 optionally and preferably has two light sources, optionally by two LEDs (light Emitting Diode) and a photoelectric detector for example. One of the LEDs emits in the infrared band and the other emits in the red band.

Figure 6:
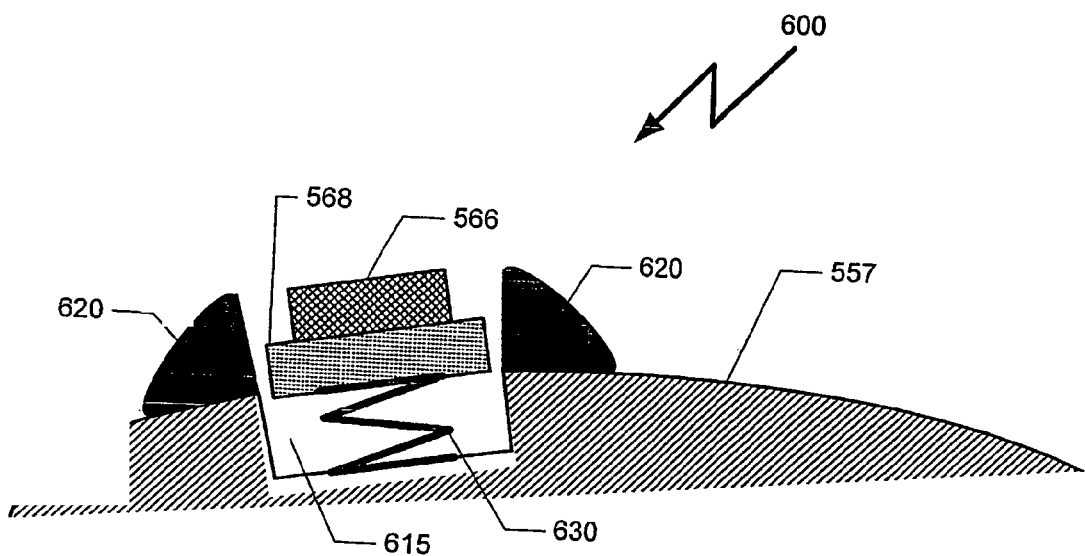
FIG. 6 is an exploded view of an exemplary device, which illustrates the installation of a SpO2 sensor.

FIG. 6 is a system diagram of an exemplary method of placement of SpO2 sensor 566 in faceplate 557 (of device 600). The two LEDs and the photoelectric detector (not shown here) of SpO2 sensor 566 are optionally installed over platform 568 which is supported by flexible support 630. Support 630 may optionally be any material which can absorb and exert pressure, including but not limited to a spring, piece of rubber, a sponge, flexible wing and so forth. Support 630 is locked in a niche 615 in faceplate 557. The edge of niche 615 is optionally and preferably surrounded by material 620, which is more preferably flexible and opaque. Material 620 may optionally be any flexible opaque substance including but not limited to rubber, sponge, flexible wings and so forth.

To perform SpO2 measurement, the user presses a finger against sensor 566, thereby pushing sensor 566 and platform 568 against flexible support 630 in the direction of faceplate 557. Flexible support 630 absorbs part of the force by moving inside niche 615 and responding to the pressure with a predetermined force, which is a result of the mechanical properties of flexible support 630. The force is predetermined to as to avoid disturbing the blood flow in the tissue. The skin of the finger (not shown) that surrounds sensor 566 is therefore pressed against flexible opaque material 620, thereby blocking light creating a dark space around the measuring area which prevents the surrounding light disturbing the measurement process. Upon depression of sensor 566, processing unit 103 (FIG. 1) initiates the SpO2 measuring thread. Processing unit 103 instructs the current drivers in analog front-end 119 (FIG. 1), which is associated with sensor 566, to force current through the LEDs alternately in sensor 566. The reflected light from the finger is received by the photo detector, which converts the photons into electronic signal. The electronic signal is fed, as one of sensors 102, to analog front end 119. Analog front-end 119 processes the analog signal and transfers the processed analog signal to A/D converter 109 (FIG. 1). The digital signal is transferred to processing unit 103 (FIG. 1), which processes the digital signal and generates the SpO2 figure. This information is then transferred to the call center via gateway 110 (FIG. 1).

The signal that is collected from the SpO2 sensor may also optionally be used for producing other heart related information. For example, processing the signal that reflects the intensity of the reflected IR light may produce information such as heart rate, PWTT, irregularity of heart rate etc.

Other exemplary embodiments may have the SpO2 sensor installed instead of the blood pressure pulse sensor (anvil 510, protrusion 520 and piezoceramic sensor 540). In this embodiment the reflected light is received from the wrist instead of the finger.

Returning to FIG. 5, device 500 may optionally have a temperature sensor 580 which is installed at the far end of long band 576. Temperature sensor 580 preferably includes a thermistor located in a metal cup and is connected via two flexible conductive wires (not shown) that run along the band into the lower case of device 500. The two wires are connected as one of sensors 102 (FIG. 1) to analog front-end 119. Analog front-end 119 converts the changes in the resistance of the thermistor into an electrical signal with magnitude proportional to the temperature of the user. The analog signal is converted into digital signal by A/D Converter 109 and transferred to processing unit 103. Processing unit 103 converts the digital signal into temperature information and sends this temperature information via gateway 110 to the call center.

Temperature sensor 580 is preferably installed in a protected solid housing. The solid housing may optionally be made of polymer, metal, gum or any material able to provide the necessary properties.

To start measuring the temperature of the user device 500 is optionally removed from the user's hand and sensor 580 is preferably pressed against the user's armpit (not shown).

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

It will be appreciated that the above descriptions are intended only to serve as examples, and that many other embodiments are possible within the spirit and the scope of the present invention.

What is claimed is:

1. A system for measuring at least one physiological parameter of a subject, comprising:
   (a) a fastening article for being fastened to the wrist of a first hand of the subject;
   (b) a measuring device for measuring at least one physiological parameter of the subject, said measuring device configured to be attached to the wrist by said fastening article;
   (c) three separate conductive areas on a surface of said measuring device, said conductive areas configured to measure electrical activity of the subject, said three conductive areas arranged in one of the following configurations:
      (i) a first conductive area configured to be in contact with at least a portion of the wrist, second and third conductive areas configured to be touched by two fingers of a second hand of the subject;
      (ii) first and second conductive areas configured to be in contact with at least a portion of the first hand and a third conductive area configured to be touched by a second hand of the subject;
   (d) a processor for continuously receiving a signal from said measuring device and for continuously converting said at least one measurement to form medical information;
   (e) a communication unit configured for at least continuously receiving said medical information from said processor and configured for at least continuously transmitting said medical information; and
   (f) a mobile gateway device configured for at least receiving said medical information from said communication unit and for at least transmitting said medical information to a remote location;
   wherein said system is configured to be carried by the subject; wherein said physiological parameter includes an electrocardiogram (ECG) signal; and
   whereby said ECG signal is extracted from said three conductive areas by using the signal of one conductive area as a reference and amplifying the differential voltage between the other two conductive areas.

2. The system of claim 1, wherein a rate of sampling determined by said processor is at least partially determined according to a type of physiological parameter being measured.

3. The system of claim 1, wherein at least one conductive area comprises an anvil.

4. The system of claim 1, wherein said physiological parameter is tonus activity.

5. The system of claim 1, wherein said the at least one physiological parameter is selected from a group consisting of heart rate; regularity in heart rate; breathing rate; arrhythmia of the heart, and overall rhythm of the heart.

6. The system of claim 1, further comprising:
   (e) a non-volatile memory for storing at least one instruction for execution by said processor.

7. The system of claim 1, wherein said communication unit also transmits a device identifier for uniquely identifying the device.

8. The system of claim 7, wherein said communication unit also receives data.

9. The system of claim 8, wherein said fastening article is a wristband.

10. The system of claim 9, further comprising a wire located at said wristband, wherein said wire is connected to said communication unit as an antenna.

11. A The system of claim 1
    wherein said communication unit is configured for at least continuously transmitting data; and
    wherein said medical information is accessible to the subject, and wherein said medical information is selected from the group consisting of: breathing rate, diastolic blood pressure, systolic blood pressure, level of sweat, oxygen saturation in the blood, glucose levels in the blood, tonus activity, Pulse Wave Transmit Time (PWTT).

12. The system of claim 1, wherein said remote location is further defined as a remote server in communication with said mobile gateway device.

13. The system of claim 12, wherein at least one of a communication link between said mobile gateway device and said remote server includes a telephone line.

14. The system of claim 1, wherein said transmitted data is analyzed at least partially automatically by said mobile gateway device.

15. The system of claim 1, wherein said measuring device and said mobile gateway device communicate bi-directionally, such that a message transmitted from said measuring device is acknowledged by said mobile gateway device, and such that if said mobile gateway device does not acknowledge correct reception of said message, said measuring device transmits said message again.

16. The system of claim 1, wherein at least one of a communication link between said measuring device and said mobile gateway device is selected from the group consisting of a wireless link and a wired link.

17. The system of claim 1, wherein said measuring device automatically performs a measurement of the physiological parameter upon manual activation of the measuring device by the subject.

18. The system of claim 17, wherein said data is automatically transmitted to said mobile gateway device upon said manual activation.

19. The system of claim 18 wherein, upon manual activation of the system by the subject, said physiological parameter is continuously converted to form medical information and said mobile gateway device continuously transmits said medical information.

20. The system of claim 1, wherein said measuring device automatically and periodically performs a measurement of the physiological parameter.

21. The system of claim 20, wherein at least one member of the group consisting of the frequency of said periodic measurement and the time period during which measurements are stored is modifiable.

22. The system of claim 20, wherein said data is automatically transmitted to said mobile gateway device if said measurement is outside of an acceptable range.

23. The system of claim 22, wherein said measurement is combined with another measurement of at least one other parameter to determine if said measurements are outside of said acceptable range.

24. The system of claim 1, wherein said mobile gateway device is configured for automatically receiving and relaying said medical information, wherein said medical information is relayed according to a packet format.

25. The system of claim 24, wherein said packet format is chosen from the group consisting of: an Internet format, GPRS (general packet radio service), an SMS (Short Message Service) format, an MMS (Multi Media Service) format, electronic mail, and Internet based messaging.

26. The system of claim 1, wherein said at least one measurement is combined with at least one other measurement of said at least one physiological parameter.

27. The system of claim 1, wherein data for all said physiological parameters are transmitted according to a security protocol for maintaining the privacy of the user.

28. The system of claim 1, further comprising a real time clock for providing at least one time tag for said at least one measurement.

29. The system of claim 1, said measuring device further comprising a memory for storing said continuously measured physiological parameters, wherein said stored data is automatically transmitted to said mobile gateway device upon manual activation.

30. A method of measuring at least one physiological parameter of a subject, with the system of claim 1, including the steps of:
    fastening the fastening article to the wrist of the first hand of the subject;
    measuring at least one physiological parameter, including an electrocardiogram (ECG) signal, of the subject by a step chosen from the group consisting of:
        i) measuring electrical activity of the subject at a first conductive area contacting at least a portion of the wrist, and measuring electrical activity at a second and a third conductive areas by touching by two fingers of a second hand of the subject;
        ii) measuring electrical activity of the subject at the first and second conductive areas configured to be in contact with at least a portion of the first hand and a third conductive area configured to be touched by the second hand of the subject; and
        iii) combinations thereof;
    extracting the ECG signal from the conductive areas by using the signal of one conductive area as a reference and amplifying the differential voltage between the other two conductive areas;
    continuously sending a signal from the measuring device to the processor, the processor continuously converting the at least one measurement to form medical information;
    continuously sending the medical information from the processor to the communication unit, the communication unit continuously transmitting the medical information to the mobile gateway device; and
    the mobile gateway device transmitting the medical information to a remote location.

31. The method of claim 30, further including the step of, if a level of at least one of the physiological parameter and the medical information is outside of an expected range, continuously transmitting said medical information.

32. The method of claim 31, wherein said expected range is modifiable.

* * * * *